United States Patent [19]

Mark et al.

[11] Patent Number: 4,895,993

[45] Date of Patent: Jan. 23, 1990

[54] PROMOTERS FOR HALOALKENE ISOMERIZATION

[75] Inventors: H. Wayne Mark, Summerville, S.C.; Richard C. Doss; Clarence R. Bresson, both of Bartlesville, Okla.

[73] Assignee: Phillips Petroleum Company, Bartlesville, Okla.

[21] Appl. No.: 244,342

[22] Filed: Sep. 15, 1988

[51] Int. Cl.$^4$ .................. C07C 17/24; C07C 17/00
[52] U.S. Cl. .................................. 570/236; 570/235; 570/202
[58] Field of Search ................................. 570/235, 236

[56] References Cited

U.S. PATENT DOCUMENTS

| | | | |
|---|---|---|---|
| 3,472,908 | 10/1969 | Harder | 570/236 |
| 4,328,381 | 5/1982 | Tabata et al. | 570/236 |
| 4,341,715 | 7/1982 | Parlman et al. | 260/455 B |

*Primary Examiner*—Howard T. Mars
*Attorney, Agent, or Firm*—Laney, Dougherty, Hessin & Beavers

[57] ABSTRACT

An isomerization of a haloalkene is conducted in the presence of a mixture of a copper compound and a trithiocarbonic acid derivative or dithiocarbonic acid derivative.

15 Claims, No Drawings

PROMOTERS FOR HALOALKENE ISOMERIZATION

BACKGROUND OF THE INVENTION

1. Field of the Invention

The present invention relates to the isomerization of haloalkenes, and more particularly, but not by way of limitation, to the isomerization of trans-1,4-dichlorobutene-2 to 3,4 dichlorobutene-1.

2. Description of the Prior Art

A number of catalytic systems have been proposed for accomplishing the isomerization of a- dichlorobutene such as trans-1,4-dichlorobutene-2. The general object of these systems has been to obtain the desired dichlorobutene in high yield at a relatively low temperature, thereby reducing the decomposition of dichlorobutene and the production of high-boiling tar by-products. A further object of these prior art systems has been to reduce the amount of catalyst necessary to effect the isomerization. Accordingly, the prior art systems have sought to produce high catalytic activity at a low concentration of catalyst.

The prior art discloses the combination of at least one of the metal salts of copper, iron, zinc and aluminum and of an auxiliary catalyst in the presence of a heated dichlorobutene to accomplish an isomerization of the dichlorobutene. For instance, U.S. Pat. No. 4,328,381 to Tabata et al. discloses a combination of a copper compound and a dithiocarbamic acid derivative containing a tertiary amine, with the copper compound being present in a concentration in the range of 0.005 to 1 weight percent and the dithiocarbamic acid derivative being present in a concentration of 0.01 to 2 weight percent. The reaction temperature is suggested as in a range of 80° to 150° C. A different system is disclosed in British Patent No. 798,889, wherein an organic amine is combined with a copper salt.

As shown by these disclosures, there is a need for a catalyst system that is effective in promoting the isomerization of haloalkenes such as trans-1,4-dichlorobutene-2 at low temperatures and at low catalyst concentrations, whereby the decomposition of the haloalkenes, the production of high-boiling by-products, and corrosion of those parts of the apparatus coming into contact with the catalyst solution are minimized.

SUMMARY OF THE INVENTION

The present invention fulfills the needs mentioned above by providing an isomerization of a haloalkene such as trans-1,4-dichlorobutene-2.

The isomerization of a haloalkene of the general formula $R-CH(Y)-CH=CH-CH_2(X)$ that is either a cis- or transisomer, where R is H, an alkyl or aryl group, X is Cl, Br or I, and Y is H, Cl, Br or I, is conducted in the presence of a catalyst mixture of a copper compound and a dithiocarbonic acid derivative or trithiocarbonic acid derivative. A process for carrying out the isomerization of such a haloalkene is also provided comprising heating the haloalkene, and adding a catalyst which comprises a mixture of a copper compound and a dithiocarbonic acid derivative or trithiocarbonic acid derivative.

The objects of the present invention include the provision of a catalyst system demonstrating high catalytic activity at low concentrations of catalyst, reduced decomposition of the haloalkene, reduced production of byproducts, and reduced corrosion of the reaction apparatus. Other objects and advantages will become apparent to a person of ordinary skill in the art upon reading the detailed description of the preferred embodiments that follows.

DETAILED DESCRIPTION OF THE PREFERRED EMBODIMENTS

A series of useful intermediates such as 3,4 dichlorobutene-1 may effectively be prepared only by the isomerization of other compounds. For example, it is known that 3,4 dichlorobutene-1 may be prepared by the isomerization of trans-1,4-dichlorobutene-2. That isomerization is carried out in accordance with the present invention by heating the trans-1,4 dichlorobutene-2, and adding a catalyst comprised of a mixture of a copper compound and a dithiocarbonic acid derivative or trithiocarbonic acid derivative to produce the 3,4 dichlorobutene-1. The selection of the aforementioned illustrative isomerization is not intended, however, as limiting the utility of the present invention, which also includes the isomerization of a haloalkene of the general formula $R-CH(Y)-CH=CH-CH_2(X)$ that is either a cis- or, preferably, a trans-isomer where R is H, an alkyl or aryl group, X is Cl, Br, or I, and Y is H, Cl, Br or I.

In accordance with the present invention, the isomerization of such other halogen substituted alkenes is carried out in the presence of a catalyst comprised of a mixture of a copper compound and a dithiocarbonic acid derivative or trithiocarbonic acid derivative. As mentioned, the catalyst mixture is effective at low temperatures and low concentrations, e.g., temperatures as low as about 50° C. and in concentrations as low as about 0.01% by weight of the haloalkene to be isomerized. Preferably, the isomerization reaction is carried out at a temperature in the range of from about 100° C. to about 150° C. and most preferably of about 120° C., using a concentration of catalyst mixture in the range of from about 0.05 to about 0.5% by weight of the haloalkene used, and most preferably of about 0.1% by weight of the haloalkene present.

The ratio of the amount of copper compound used to the amount of dithiocarbonic acid derivative or trithiocarbonic acid derivative used can vary from about 0.1 to about 10 parts by weight copper compound per part by weight dithiocarbonic acid derivative or trithiocarbonic acid derivative. Preferably, the catalyst mixture is comprised of from about 0.2 to about 5 parts by weight copper compound per part by weight dithiocarbonic acid derivative or trithiocarbonic acid derivative. Most preferably, the catalyst mixture comprises equal parts by weight of copper compound and dithiocarbonic acid derivative or trithiocarbonic acid derivative. The isomerization is conducted, further, at pressures in the range of from about 0 psig to about 1000 psig, and is preferably carried out at pressures from about 5 psig to about 100 psig.

The copper compounds which may be used as catalysts for the isomerization include both organic and inorganic compounds. Examples of such compounds are cuprous bromide, cuprous iodide, cuprous acetate, copper naphthenate and cuprous chloride, with cuprous chloride being the most preferred.

The preferred acid derivatives of the present invention are characterized by the formulas

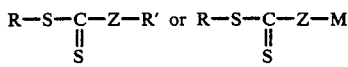

wherein R and R' are the same or different and respectively represent an alkyl, aryl, alkenyl, or carboxyalkyl group, M represents an ammonium group or alkali metal, and Z is S or O. Typical derivatives include sodium butyl trithiocarbonate, S-allyl-S'-n-butyl trithiocarbonate, and sodium carboxymethyltrithiocarbonate.

The trithiocarbonic acid derivatives are prepared, for example, by the reaction of carbon disulfide with a mercaptan such as butyl mercaptan in an alkaline environment to give an intermediate trithiocarbonate salt, which intermediate is subsequently treated with a halide compound such as allyl chloride to produce a trithiocarbonate ester such as S-allyl-S'-n-butyl trithiocarbonate. The conditions under which such derivatives may be prepared are discussed more fully in U.S. Pat. No. 4,341,715 to Parlman et al. which is incorporated herein and made part hereof by reference, but generally involve placing the mercaptan in an alkaline solution with stirring for approximately 1 to 2 hours at temperatures of about 25° to 100° C. and at pressures of 0 to 500 psig, adding the carbon disulfide with stirring for another 1 to 2 hours, and then adding the halide compound over a period of from 1 to 10 hours. After cooling, separation and isolation of the trithiocarbonic acid derivative are undertaken.

The procedure for the production of the dithiocarbonic acid derivatives of the present invention is well-known in the art, and is generally that followed in the preparation of trithiocarbonic acid derivatives, except that alcohols are reacted with carbon disulfide rather than the mercaptans used for producing the trithiocarbonic acid derivatives.

The present invention may be illustrated by the following example.

EXAMPLE

A comparative test of a dithiocarbamate-promoted isomerization of trans-1,4-dichlorobutene-2 and a trithiocarbonate-promoted isomerization of the same compound was conducted. In each run the charge to the reaction vessel consisted of 100 grams of trans-1,4-dichlorobutene-2, 0.1 grams of cuprous chloride and 0.1 grams of the appropriate auxiliary catalyst. The dithiocarbamate used was S-allyl-n-butyl dithiocarbamate, while the trithiocarbonate selected was S-allyl-S'-n-butyl trithiocarbonate.

Initially the trans-1,4-dichlorobutene-2 was heated at 120° C. and a pressure of about 1 atmosphere for a period of about 3 hours, whereupon the cuprous chloride and dithiocarbamate or trithiocarbonate were added. The contents of the vessel were sampled immediately before the catalyst addition, immediately after addition, and at approximately 30 minute intervals thereafter.

Analysis of the samples thus taken indicated the compositions described in Table I. The dithiocarbamate S-allyl-n-butyl dithiocarbamate is signified "ABD" in Table I, whereas S-allyl-S'-n-butyl trithiocarbonate is represented by the "ABT" notation.

TABLE I

| Promoter System | Sample Time | Trans-1,4- Dichlorobutene-2 | Cis-1,4- Dichlorobutene-2 | 3,4-Dichlorobutene-1 |
|---|---|---|---|---|
| CuCl/ABD | Before Addition | 78.1 | 7.1 | 12.4 |
|  | After Addition | 78.0 | 7.0 | 13.0 |
|  | 30 min. | — | — | — |
|  | 60 min. | 68.2 | 7.0 | 22.2 |
|  | 90 min. | 68.5 | 7.1 | 22.0 |
|  | 120 min. | 68.8 | 7.2 | 21.8 |
|  | 150 min. | — | — | — |
| CuCl/ABT | Before Addition | 83.5 | 7.5 | 7.2 |
|  | After Addition | 83.1 | 7.5 | 7.9 |
|  | 30 min. | 75.5 | 7.1 | 15.4 |
|  | 60 min. | 72.5 | 7.1 | 19.0 |
|  | 90 min. | 70.1 | 7.1 | 21.0 |
|  | 120 min. | 68.5 | 7.2 | 22.8 |
|  | 150 min. | 68.0 | 7.2 | 22.5 |

As Table I demonstrates, the present invention promotes the isomerization of the haloalkene trans-1,4-dichlorobutene-2 with an effectiveness that is comparable at the catalyst concentration and temperature of the Example to that of the copper-dithiocarbamate compound system.

The present invention, therefore, is well adapted to carry out the objects and attain the ends and advantages mentioned as well as those inherent therein. While reasonable variations and modifications which will become apparent to those skilled in the art can be made, such changes and modifications are included within the spirit of this invention as defined by the appended claims.

What is claimed is:

1. A process for isomerizing a haloalkene of the general formula R—CH(Y)—CH=CH—CH$_2$(X) that is either a cis- or trans-isomer where R is H, an alkyl or aryl group, X is Cl, Br, or I and Y is H, Cl, Br or I, comprising the steps of:
   heating the haloalkene; and
   adding a catalyst comprised of a mixture of a copper compound and a dithiocarbonic or trithiocarbonic acid derivative.

2. The isomerization of claim 1 wherein trans-1,4-dichlorobutene-2 is isomerized into 3,4-dichlorobutene-1.

3. The isomerization of claim 1 wherein said copper compound and said acid derivative are present in said catalyst mixture in equal parts by weight.

4. The process of claim 1 wherein said copper compound is selected from the group consisting of cuprous bromide, cuprous iodide, cuprous acetate, copper naphthenate and cuprouc chloride.

5. The process of claim 1 wherein said second compound is a compound having the formula

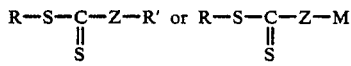

wherein R and R' are the same or different and are each an alkyl, aryl, alkenyl, or a carboxyalkyl group, M is ammonium or an alkali metal, and Z is S or O.

6. The process of claim 5 wherein said second compound is selected from the group consisting of sodium butyl trithiocarbonate, S-allyl-S'-n-butyl trithiocarbonate, and sodium carboxymethyltrithiocarbonate.

7. The process of claim 1 wherein said catalyst comprises a mixture of cuprous chloride and S-allyl-S'-n-butyl trithiocarbonate.

8. The process of claim 1 wherein said haloalkene is heated to a temperature of about 120° C.

9. The process of claim 1 wherein said haloalkene is heated to a temperature in the range of from about 100° C. to about 150° C.

10. The process of claim 1 wherein said catalyst is present in a concentration of about 0.1% by weight of the haloalkene present.

11. The process of claim 1 wherein said catalyst is present in a concentration in the range of from about 0.05% to about 0.5% by weight of the haloalkene present.

12. The process of claim 1 wherein said reaction is carried out at a pressure in the range of from about 0 psig to about 1000 psig.

13. The process of claim 1 wherein said reaction is carried out at a pressure in the range of from about 5 psig to about 100 psig.

14. The process of claim 1 wherein said copper compound is present in said mixture in the range of from about 0.1 to about 10 parts by weight copper compound per part by weight of said acid derivative therein.

15. The process of claim 1 wherein said copper compound is present in said mixture in the range of from about 0.2 to about 5 parts by weight copper compound per part by weight of said acid derivative therein.

* * * * *